United States Patent

Kobayashi

[11] Patent Number: 5,864,597
[45] Date of Patent: Jan. 26, 1999

[54] X-RAY COMPUTED TOMOGRAPHY DEVICE AND METHOD

[75] Inventor: Tadaharu Kobayashi, Tochigi-ken, Japan

[73] Assignee: Kabushiki Kaisha Toshiba, Kawasaki, Japan

[21] Appl. No.: 826,505

[22] Filed: Apr. 3, 1997

[30] Foreign Application Priority Data

Apr. 3, 1996 [JP] Japan .................................. 8-081534

[51] Int. Cl.$^6$ .......................................................... A61B 6/03
[52] U.S. Cl. .................................................. 378/4; 378/15
[58] Field of Search ........................... 378/15, 4, 19, 378/20, 901

[56] References Cited

U.S. PATENT DOCUMENTS 4,789,929  12/1988  Nishimura et al. .
5,270,923  12/1993  King et al. .
5,485,493  1/1996  Heusher et al. ........................... 378/15
5,544,212  8/1996  Heuscher ............................. 378/901 X

OTHER PUBLICATIONS

Basic Principles and Clinical Applications of Helical Scan, pp. 121–130, T. Katakura, et al., "Performance Evaluation of the Helical Scan Method" no date.

Primary Examiner—David P. Porta
Attorney, Agent, or Firm—Oblon, Spivak, McClelland, Maier & Neustadt, P.C.

[57] ABSTRACT

An x-ray computed tomography device and method for automatically setting scan conditions in order to substantially equalize a designated slice thickness with an effective slice thickness. The device according to the present invention preferably employs a helical scan method. While a rotatable frame portion is continuously rotated in a scanning operation, a detected object can be moved in a body longitudinal direction. A slice thickness designated by an x-ray optical mechanism including a slit and a beam trimming machine and a scan pitch of the helical scan are controlled so that the designated and effective slice thicknesses are substantially equal.

32 Claims, 7 Drawing Sheets

X-RAY COMPUTED TOMOGRAPHY DEVICE AND METHOD

BACKGROUND OF THE INVENTION

1. Field of the Invention

The present invention relates to an x-ray computed tomography device and method, and more particularly to a helically scanning x-ray computed tomography device and method where the effective slice thickness may be adjusted.

2. Discussion of the Background

Figure 6:
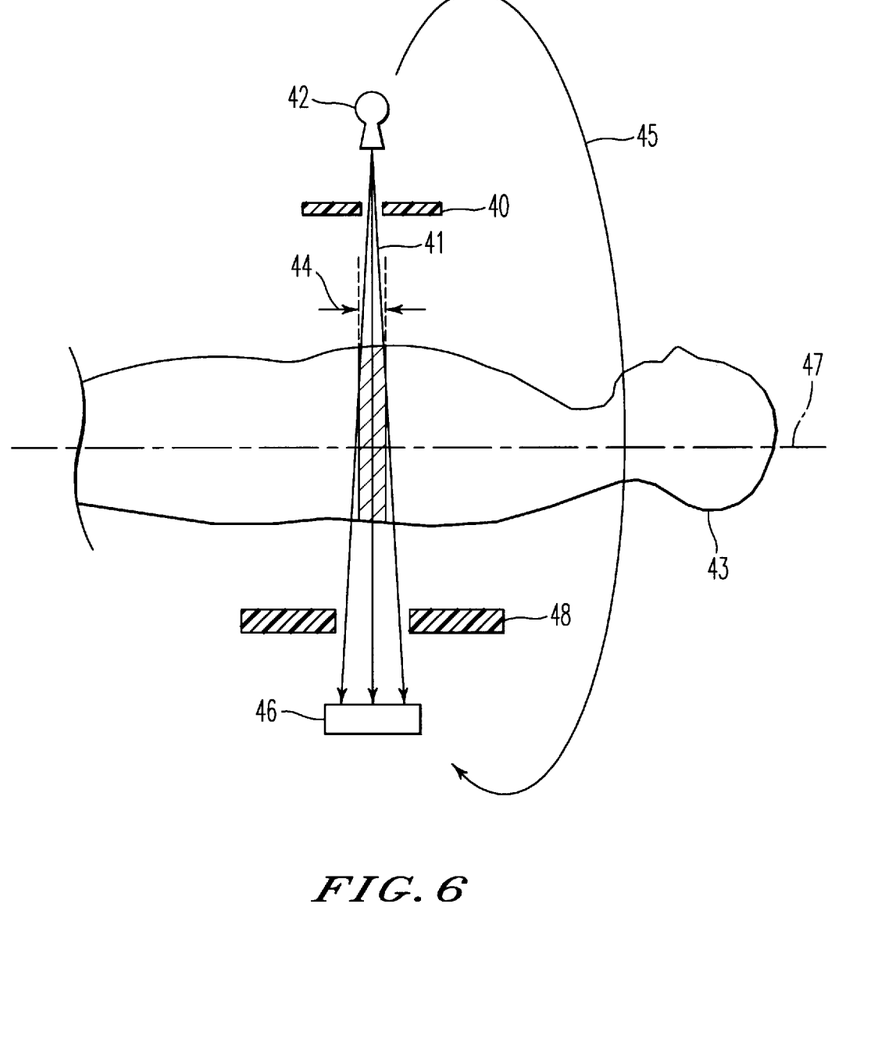
FIG. 6 illustrates a scanning operation of a conventional x-ray CT device.

As shown in FIG. 6, an x-ray computed tomography device (hereinafter, it is referred as "x-ray CT device") comprises an x-ray tube 42 for irradiating a beam of x-rays 41 and a detector 46 for detecting x-rays passed through a detected object, such as patient 43, wherein the detector 46 is positioned at a side opposite to the x-ray tube 42 with respect to the detected object and a tomography image can be obtained by rotating the x-ray tube 42 integrally with the detector 46 around the detected object (shown by arrow 45) in order to scan the detected object and reconstruct the projected data.

Such a tomographic image obtained by an x-ray CT device contains area information of the x-ray beam 41 having a predetermined width along a body longitudinal direction of the detected object, wherein the x-ray beam 41 passes through the detected body and is irradiated on detector 46 with a predetermined width along the same direction. The area is called the slice thickness and is indicated as 44. In general, slice thickness 44 is determined by a width of the x-ray beam 41 at a rotational center 47. The slice thickness is also determined by setting an x-ray optical mechanism including a beam trimming machine 40 located between x-ray tube 42 and the detected object and a beam trimming machine 48 located between the detected object and detector 46. In other words, a desirable slice thickness can be set by changing the settings of the x-ray optical mechanism. In an x-ray CT device utilized in the medical industry, a desirable slice thickness can be selected from a plurality of predetermined values (for example, one value, such as 2 mm, is selected from a set of values, i.e., 1 mm, 2 mm, 5 mm, 7 mm and 10 mm) by considering the desired diagnostic purpose and scanning period. Then, the x-ray optical mechanism is set to match the selected slice thickness.

Figure 7:
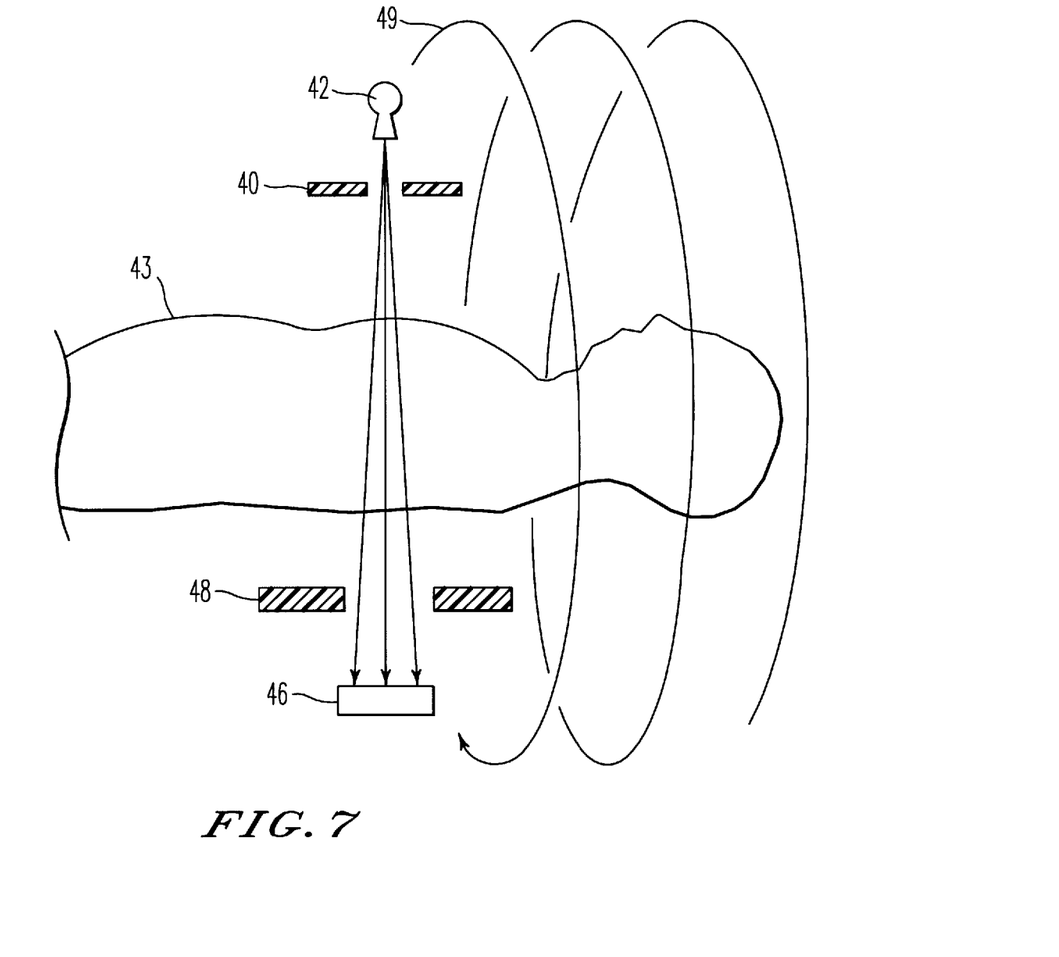
FIG. 7 illustrates a helical scanning operation of a conventional x-ray CT device.

As shown in FIG. 7, in a conventional x-ray CT device employing a helical scan method, a rotatable frame on which an x-ray tube 42 and a detector 46 are mounted is continuously rotated by connecting with a frame fixed portion through a slipping device (not shown). A bed on which a detected object is disposed is moved along a body longitudinal direction in order to scan helically, indicated as 49, and then projection data of the scanned detected object is obtained rapidly. In such a conventional x-ray CT device employing a helical scan method, actual data is interpolation processed in order to reconstruct a tomographic image at a slice portion. Therefore, an effective slice thickness of the tomographic image obtained by reconstruction (an effective slice thickness can be determined by a known method) is likely to be thicker than a thickness selected by the x-ray optical mechanism. The thicker an effective slice thickness becomes, the lower the spatial resolution capability becomes.

SUMMARY OF THE INVENTION

An object of the present invention is to provide a computed tomography device and method having improved spatial resolution.

Another object of the present invention is to provide an x-ray computer tomography device and method, wherein a preferable scanning condition is automatically set to substantially equalize a selected slice thickness with an effective slice thickness.

These and other objects are achieved by a device having a slice thickness selection device, an effective slice thickness determination device and a device for substantially equalizing the selected slice thickness and the effective slice thickness. The device for substantially equalizing the selected slice thickness and the effective slice thickness may consist of all or one of an x-ray beam slit, an x-ray beam trimmer and a scan pitch control device. The selected slice thickness can be adjusting by varying the widths of the openings of the slit and trimming device or by adjusting the scan pitch.

The device for substantially equalizing the selected slice thickness and the effective slice thickness can determine an increasing ratio to perform the substantial equalizing. The increasing ratio may be determined based upon a reconstruction method chosen. For example, if a 360° interpolation processing method is selected, the selected slice thickness is reduced by approximately 30–40%.

The device according to the invention is effective when a helical scan device is used.

The effective and selected scan thicknesses may be equalized within approximately ±10% and achieve the beneficial effects of the invention.

The objects of the invention are also achieved by a computed tomography method where a designated slice thickness is set to be substantially equal to an effective slice thickness. This may be accomplished using an increasing ratio. The substantial equalization may be carried out by adjusting x-ray beam parameters and/or by adjusting a scan pitch.

The substantial equalization may be also dependent upon the reconstruction method utilized. The selection of the reconstruction method may be used in determining the value of the increasing ratio. For example, if a 360° interpolation processing method is selected, the selected slice thickness is reduced by approximately 30–40%.

BRIEF DESCRIPTION OF THE INVENTION

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
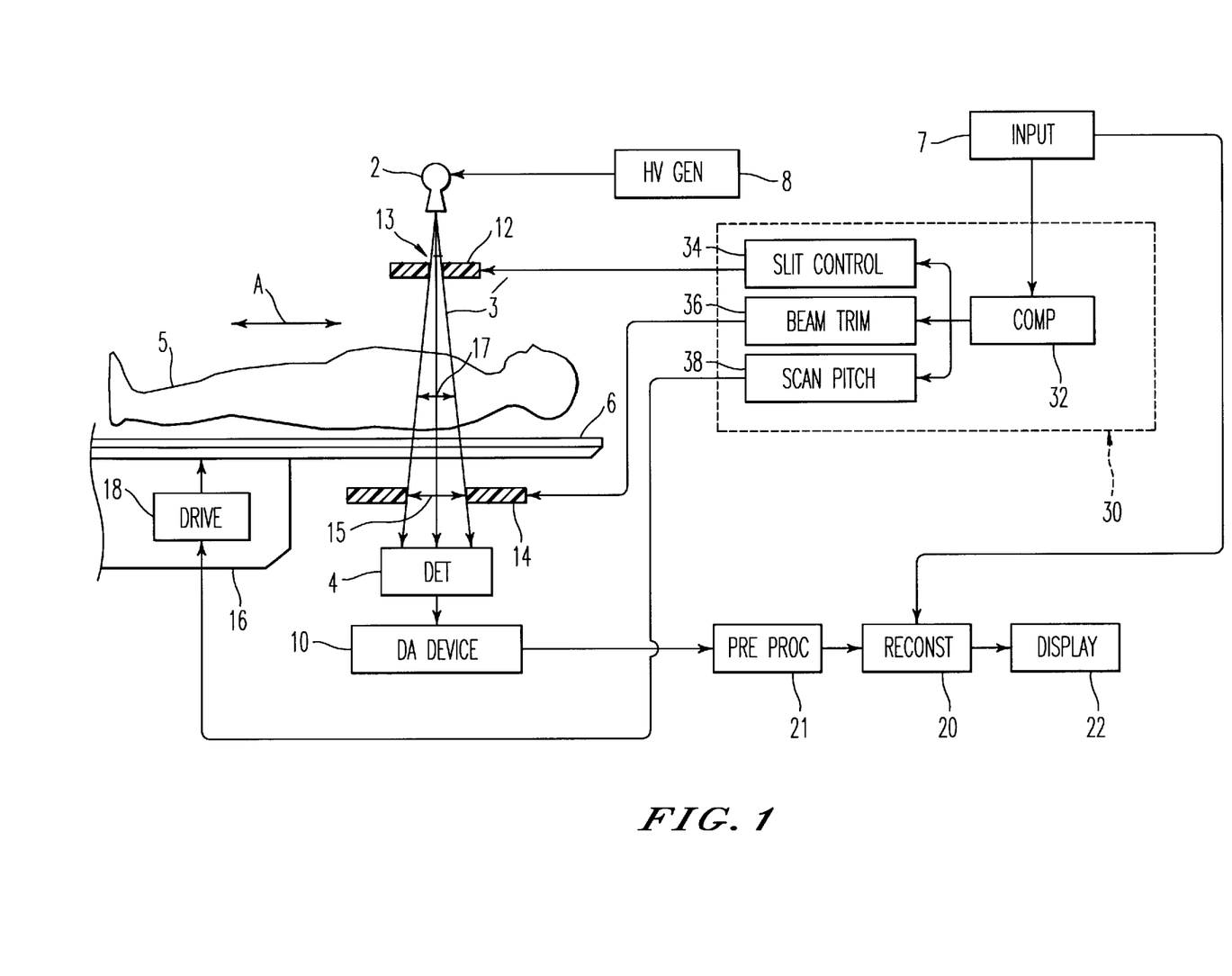
FIG. 1 is a block diagram of one embodiment of an x-ray computed tomography device according to the present invention.

Referring now to the drawings, where like reference numerals designate corresponding parts throughout the views, and more particularly to FIG. 1 which is a block diagram of the x-ray computed tomography (CT) device according to a first embodiment of the present invention. The embodiment is suitable to an x-ray CT device referred to as the third generation type in which a rotatable frame (not shown) having an x-ray tube 2 and a detector 4 rotates around a detected object, such as patient 5 disposed on bed 6. The x-ray CT device according to the first embodiment preferably employs a helical scan method. That is, the rotatable frame is connected to a fixed frame portion (not shown) through a slipping device so as to rotate continuously, and the bed 6 is moved in a body longitudinal direction of the detected object (as shown by arrow A) while the rotatable frame is continuously rotating in an exposure operation. On the other hand, the rotatable frame portion and the fixed frame portion may be moved in the direction of the arrow A with respect to the detected object, such as patient 5, in order to scan helically.

The x-ray tube 2 produces x-rays by supplying high voltage electric power from a high voltage generator 8 and irradiates a fan-shaped x-ray beam 3 on the detected object disposed on bed 6. The x-ray beam 3 has a predetermined thickness with respect to the body longitudinal direction of the detected object. The predetermined thickness can be determined by a slit 12 having an opening portion 13 and being located between the x-ray tube 2 and the detected object.

The detector 4 includes a plurality of detecting elements arranged along an arc line of which a center point corresponds to a focal point of the x-ray beam 3 irradiated from the x-ray tube 2. Each detecting element detects an x-ray beam transmitted through the detected object 5 and has enough thickness along the body longitudinal direction of the detected object to detect to an x-ray beam having the maximum slice thickness set by the device. While the rotatable frame portion rotates with a predetermined angle, the detector 4 converts intensity of detected x-rays into electric signals (such as electric current) and outputs the signal. An output terminal of the detector 4 is connected to data acquisition device 10.

The data acquisition device 10 converts the electric signal output from the detector 4 into a voltage signal and the voltage signal is A/D converted. An obtained digital signal is transmitted to a preprocessing device 21 described hereinafter. The preprocessing section 21 preprocesses the digital signal such as adjusting the light intensity of irradiated x-ray beam reference adjustment, logarithmic conversion and adjusting sensibility dispersion among detecting elements (such preprocessed data is referred to as actual data). An output terminal of the preprocessing device 21 is connected to an image reconstruction device 20.

The image reconstruction device 20 reconstructs a tomographic image of the detected object 5 by reconstruction computation including, for example, a convolution operation and a back projection operation with respect to data output from the data acquisition device 10. Image reconstruction device 20 produces pseudo-actual data by interpolation-processing the actual data at the specific slice position for reconstructing a tomographic image of the detected object 5.

The production of the pseudo-actual data by the interpolation process is dependent on conventional interpolation methods, such as a 360° interpolation process method or a 180° interpolation method. In the embodiment, it is possible to select and operate one of these two interpolation process methods, although other methods may be used. The 360° interpolation process method will be explained to illustrate the invention.

Figure 2A:
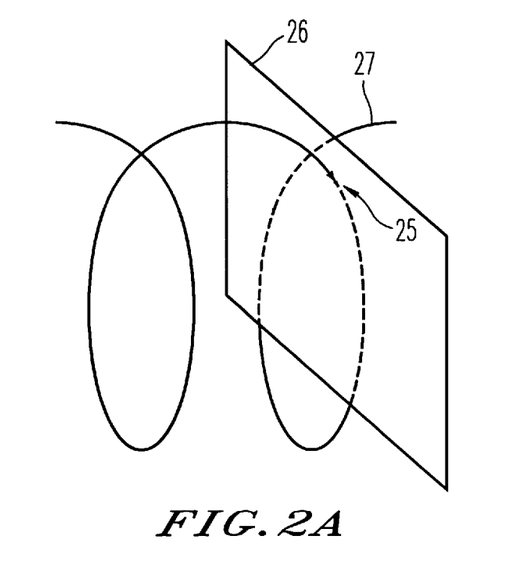
FIGS. 2A and 2B illustrate an interpolation process used in the device of FIG. 1.
Figure 2B:
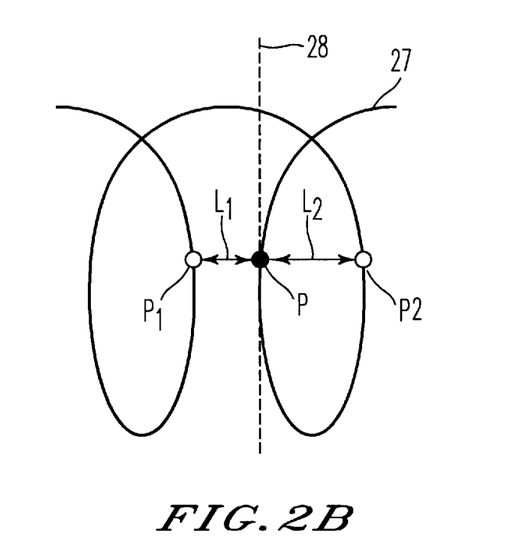

In a helical scan method, as shown in FIG. 2A, there is only data of one projected angle corresponding to a slice position. Point 25 represents projected data on the slice position 26 intersecting with the path 27 of the x-ray source in the helical scan. In order to reconstruct a tomographic image of the specific slice position, pseudo-actual data P is calculated based on data located at the front and rear positions with respect to the specific slice position at the same projection angle in accordance with the following equation:

$$P = (L2 \cdot P1 + L1 \cdot P2)/(L1 + L2)$$

where P1 and P2 are acquired actual data and L1 and L2 are a distance between a reconstruction position and a position where actual data P1 and P2 are acquired, respectively. FIG. 2B illustrates the positions P1 and P2 and the distances L1 and L2 at a reconstruction position 28. Such a calculation is repeated for a plurality of projection angles in order to acquire the pseudo-actual data for the whole angle 360°.

An output terminal of a reconstruction section 20 is connected to display 22. Display 22 displays a tomographic image of the detected object 5 corresponding to the data output from the reconstruction section 20 and can be, for example, a video display terminal.

The effective slice thickness will now be explained. As described above, the pseudo-actual data can be acquired from data actually measured through an interpolation process. The data actually measured includes information regarding transmission percentage of an x-ray beam having a predetermined beam width set, for example, by a x-ray optical mechanism, and transmitted through a detected object. Therefore, the pseudo-actual data includes information regarding the transmission percentage of the x-ray beam having a width wider than the above predetermined beam width transmitted through a detected object due to the interpolation process. It reduces the resolution capability of a reconstructed image along the body longitudinal direction. According to the present invention, an increasing ratio of an effective slice thickness compared to the predetermined slice thickness is determined beforehand in accordance with the following experiments.

Figure 3A:
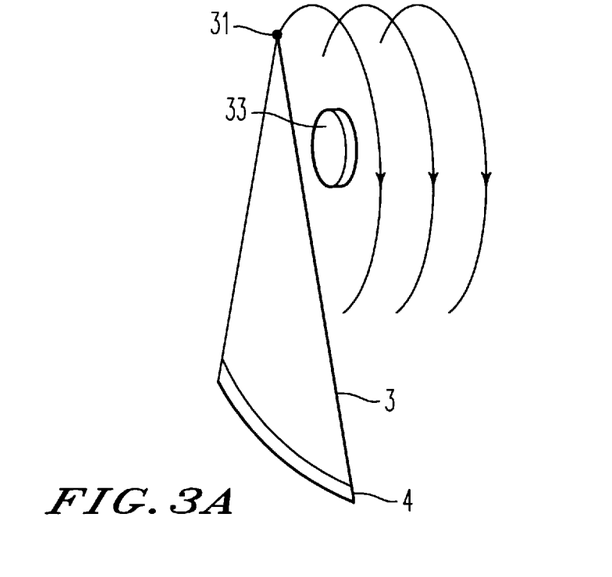
FIG. 3A is a diagram of a scanning operation.
Figure 3B:
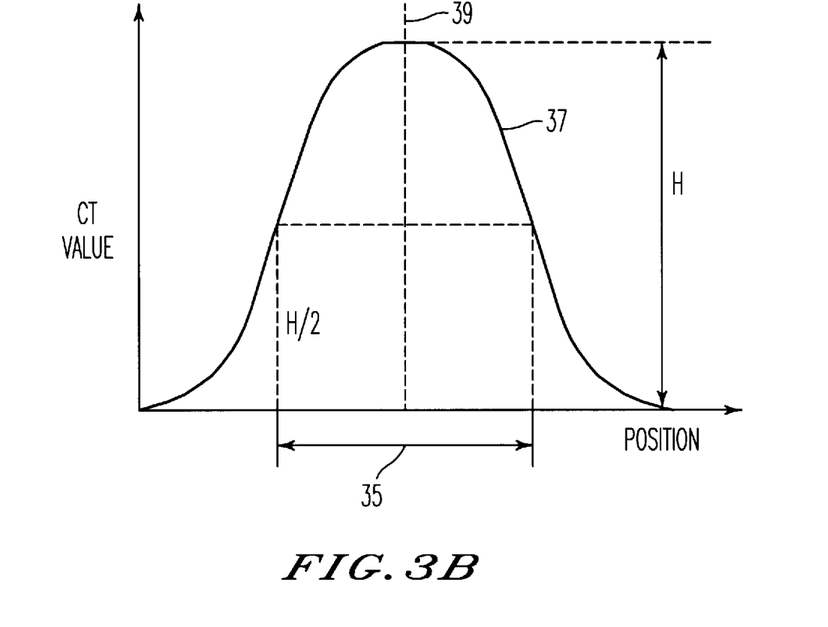
FIG. 3B is a diagram of a slice profile of the scanning operation of FIG. 3A.

As shown in FIG. 3A, a phantom such as, for example, a coin-shaped phantom 33, is helically scanned and its tomographic image is reconstructed by an interpolation process. Also illustrated in FIG. 3A is the position 31 of the x-ray source that emits an x-ray beam 3 onto detector 4. A slice profile showing the distribution of CT values of the tomographic image of the phantom obtained by the reconstruction is obtained. FIG. 3B shows one example of such a slice profile. In FIG. 3B, the horizontal axis shows a position of a detected object (coin phantom 33) in a body longitudinal direction and a vertical axis shows the CT amount corresponding to each position. Also shown in FIG. 3B is a width 35 of the profile at a height (H/2) equal to half of the maximum height H of the slice profile 37, which is designated as an effective slice thickness. The center of the coin phantom 33 in the profile 37 is given as 39.

The increasing ratio of an effective slice thickness is calculated in accordance with the following equation:

increasing ratio (%)=effective slice thickness/slice thickness set by the x-ray optical mechanism×100

For example, based on such experimental procedure, in the case of the 360° interpolation method, an effective slice thickness is approximately 1.3–1.4 times as thick as a slice thickness determined by the x-ray optical mechanism (slit 12 and/or beam trimming machine 14). In the case that the slice thickness is 2 mm, the effective slice thickness is approximately 2.6–2.8 mm. In the case of the 180° interpolation method, an effective slice thickness is approximately 1.1–1.2 times as thick as the designated slice thickness. A pitch of a helical scan is designated the same as the slice thickness specified by the x-ray optical mechanism.

An increasing ratio of an effective slice thickness is determined beforehand. The effective slice thickness or increasing ratio is stored in a data base (not shown) of the control device 30 of the device of FIG. 1.

A control device 30 controls the slice thickness specified by the x-ray optical mechanism and a helical scan pitch of a helical scan operation in accordance with a slice thickness selected by an operator and a selected interpolation processing method. Control device 30 includes a computing device 32, a slit controlling device 34, a beam trimming device 36 and a scan pitch control device 38. The slit control device 34, the beam trimming section 36 and the scan pitch control section 38 are connected to an output terminal of the computing device 32. The output terminal of the slit control device 34 is connected to the slit 12, the output terminal of the beam trimming control device 36 is connected to the beam trimming machine 14 and the output terminal of the scan pitch control device 38 is connected to a driving section 18. The driving section 18 is provided in a bed controller 16 so that the bed 6 can be slid along the direction as shown by the arrow A.

Data concerning the scan pitch and the desired interpolation processing method are input to computing device 32 through an input 7, which can be, for example, a keyboard or a software menu. Computing device 32 then determines the proper settings for the slit 12, beam trimmer 14 and bed controller 16 and instructs slit controlling device 34 to control the gap width 13 of slit 12, instructs beam trimming device 36 to control the gap width 15 of trimmer 14, and instructs scan pitch control device 38 to control the bed controller 16 to move bed 6 to produce the desired scan pitch. The effective slice thickness may be stored in computing device 32 providing rapid access to this information.

The elements of control device 30 (32, 34, 36 and 38) can be implemented as discrete circuits or the elements can be combined in a microprocessor-based system. Also, the elements of control device 30 may be implemented in software.

Figure 4:
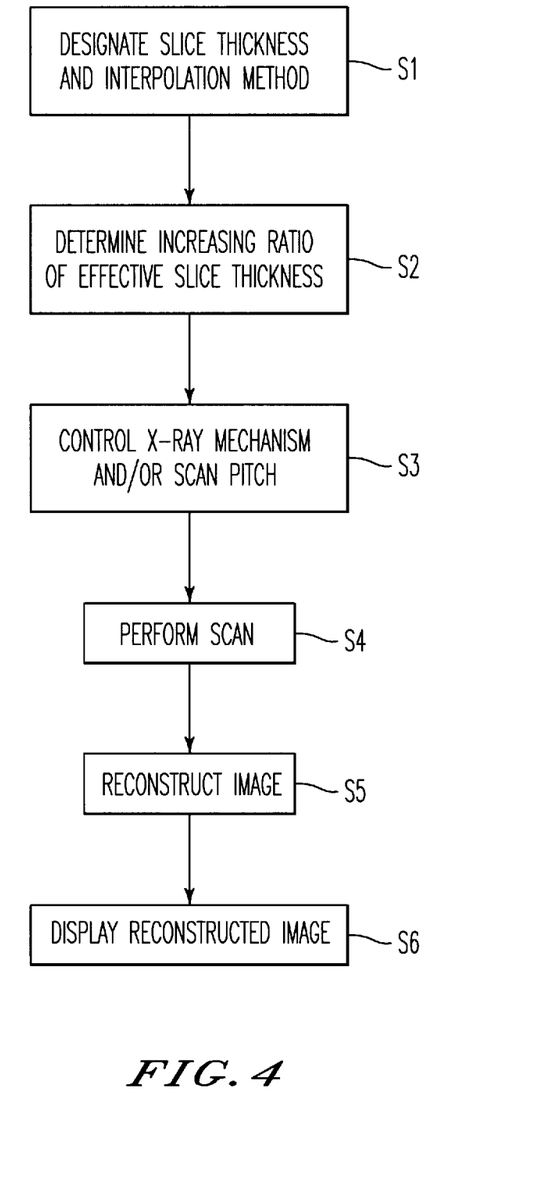
FIG. 4 is a flow-chart for explaining an operation of the embodiment of FIG. 1.

The operation of the device according to the present invention will now be explained with reference to the flow chart of FIG. 4. In step S1, an operator selects a slice thickness and an interpolation process method. These selections are entered via input 7. The inputted data is transmitted to the computing device 32 in the control device 30. Regarding the interpolation process methods, in this embodiment the operator can select either the 360° interpolation processing method or the 180° interpolation processing method. On the other hand, control device 30 may automatically select a proper interpolation process method in accordance with the scanning conditions such as a selected slice thickness. In FIG. 4, a selected slice thickness and a selected interpolation processing method are referred to as "designated slice thickness" and "designated interpolation processing method," respectively.

In step S2, the computing device 32 determines an increasing ratio of an effective thickness obtained, for example, by the experiment described above in FIGS. 3A and 3B. Computing device 32 can retrieve this information from storage, since it is preferred that it is determined beforehand. The determined increasing ratio of the effective slice thickness, or other instruction, is output from the computing device 32 to the slit control device 34, the beam trimming control device 36 and the scan pitch control device 38.

In step S3, the slit control device 34, the beam trimming control device 36 and/or the scan pitch control device 38 are operated. The slit control section 34 controls an opening width 13 of the slit 12 based on the designated slice thickness and the increasing ratio of the effective slice thickness. For example, if an operator selects 2 mm as a slice thickness and 360° interpolation process method in step S1, the computing section 32 calculates 30% as the increasing ratio of the effective slice thickness in step S2, the slit control section 34 controls an opening width (x=1.5 mm) of the slit 12 (1.3x=2, x=1.5). The beam trimming control device 36 controls the opening width 15 of the beam trimming machine 14 for the desired slice thickness, similar to the slit control device 34. The opening width 15 may be controlled using distance proportionality of the focus center distance and focus detector distance. The width 17 is equal to the width 15 multiplied by the ratio of the distance from the x-ray source 2 to the beam trimming device 14 to the distance from the x-ray source 2 to where the slice thickness is determined, i.e. the rotational center in this example. Under these controls, the geometric position of the x-ray optical mechanism is preferably adjusted and then a slice thickness is designated.

The scan pitch control section 38 controls the helical scan pitch in the helical scan operation. An inherent scanning condition of the helical scan method, for example, a moving speed (mm/sec) of a detected object (bed 6) per unit time is considered. According to the present invention, a helical scan pitch, that is, while the rotatable frame portion rotates once, a moving amount (mm/revolutions) for moving a detected object 5 (bed 6) along the body longitudinal direction is specified as one of inherent scan conditions. The helical scan pitch is designated as the moving amount of the rotatable frame portion relative to the detected object 5 (bed 6). For example, if the rotatable frame portion is moved simultaneously with rotating around the detected object 5 (bed 6), a moving amount of the rotatable frame portion along a body longitudinal direction per one revolution is designated as the helical scan pitch.

In this embodiment of the present invention, the above helical scan pitch is equalized to a slice thickness determined by the x-ray optical mechanism. For example, if an operator selects 2 mm as a slice thickness and the 360° interpolation processing method in step S1, the increasing ratio of the effective slice thickness is calculated as 30% by the computing section 32, the slice thickness designated by the x-ray optical mechanism is 1.5 mm in step S2, and the helical scan pitch is designated at 1.5 mm/revolution. The scan pitch control section 38 controls driving section 18 in bed controller 16 in accordance with the determined helical scan pitch in step S4 (helical scanning operation).

In step S4, a helical scan operation is conducted. While the rotatable frame portion is continuously rotated simultaneously with irradiating the x-ray beam 3 on detected object 5 and moving the bed 6 continuously, actual data of detected object 5 from multiple directions are acquired. After scanning detected object 5 from the scan beginning point to the scan finishing point, the scan operation is finished and the method proceeds with step S5.

In step S5, an operator designates a reconstruction point through input 7 (or another unshown input, if desired). The designation can occur at an earlier time in the device operation. After designating the reconstruction point, the reconstruction section 20 produces pseudo-actual data in the reconstruction point by the above described interpolation process method and reconstructs a tomographic image of the detected object 5 by a reconstruction computation. For standard scanning operations, the reconstruction point may be automatically selected.

According to steps S2 and S3, scan conditions (slice thickness specified by the x-ray optical mechanism and helical scan pitch in the helical scanning operation) are designated in order to cancel the increased amount of the effective slice thickness. The reconstructed tomographic image has the effective slice thickness substantially equal to the slice thickness previously designated.

In step S6, the reconstructed tomographic image is displayed on the display section 22. An observer can observe a tomographic image of which an effective slice thickness is equal or almost equal to a slice thickness previously designated.

The device according to the invention achieves a matching, or near matching of the designated and effective slice thickness by controlling the slit 12 and beam trimming device 14 widths and the helical scan pitch. This provides the optimal matching conditions. However, matching, or near matching of the designated and effective slice thickness can be obtained by other means as described below.

A second embodiment of the invention will now be described where the scan thickness is determined using only either or both of slit 12 and beam trimming device 14. Slit 12 is used primarily to control the slice thickness while beam trimmer 14 is used primarily to eliminate a scatter component from the detected object. The scatter component is more significant when the slice thickness is small or at the minimum value, i.e., 1 mm for a set of 1, 2, 5, 7, and 10 mm slice thickness values as in the present example. Thus, the slice thickness can be controlled using only the slit 12. In this case the beam trimming device 14 may be set at a maximum amount or at a value that does not significantly affect the slice thickness determined by slit 12 but works to eliminate some or all of the scatter component.

Beam trimming device 14 is effective to control the slice thickness when the scan pitch is small or at its minimum value. When beam trimming device 14 is used alone, slit 12 may be set at or near its minimum value.

The second embodiment of the present invention controls only a slice thickness specified by the x-ray optical mechanism, i.e., control either slit or trim. Here, the helical scan pitch is set to an amount corresponding to a slice thickness designated by an operator.

In a third embodiment of the present invention, the slice thickness is controlled using only the helical scan pitch of a helical scan. Regarding a slice thickness specified by the x-ray optical mechanism, the slice thickness corresponds to a slice thickness designated by an operator. For example, if an effective slice thickness is increased 30%, a helical scan pitch becomes smaller in order to cancel the increased amount. In this case the slit 12 and the beam trimming device 14 may be set at or near their respective minimum values.

As described above, according to the present invention, if a desirable slice thickness is designated, some scan conditions (depending on x-ray optical mechanism and scan pitch) are automatically set in order to substantially equalize the selected slice thickness with the effective slice thickness. Thereby, the x-ray mechanism according to the invention can be operated without considering the increased amount of the effective slice thickness, allowing an operator to reduce his work. In addition, the spatial resolution capability caused by increasing the effective slice thickness compared to a designated slice thickness can be prevented from being reduced so that the accuracy of diagnosing an image can be improved.

Figure 5:
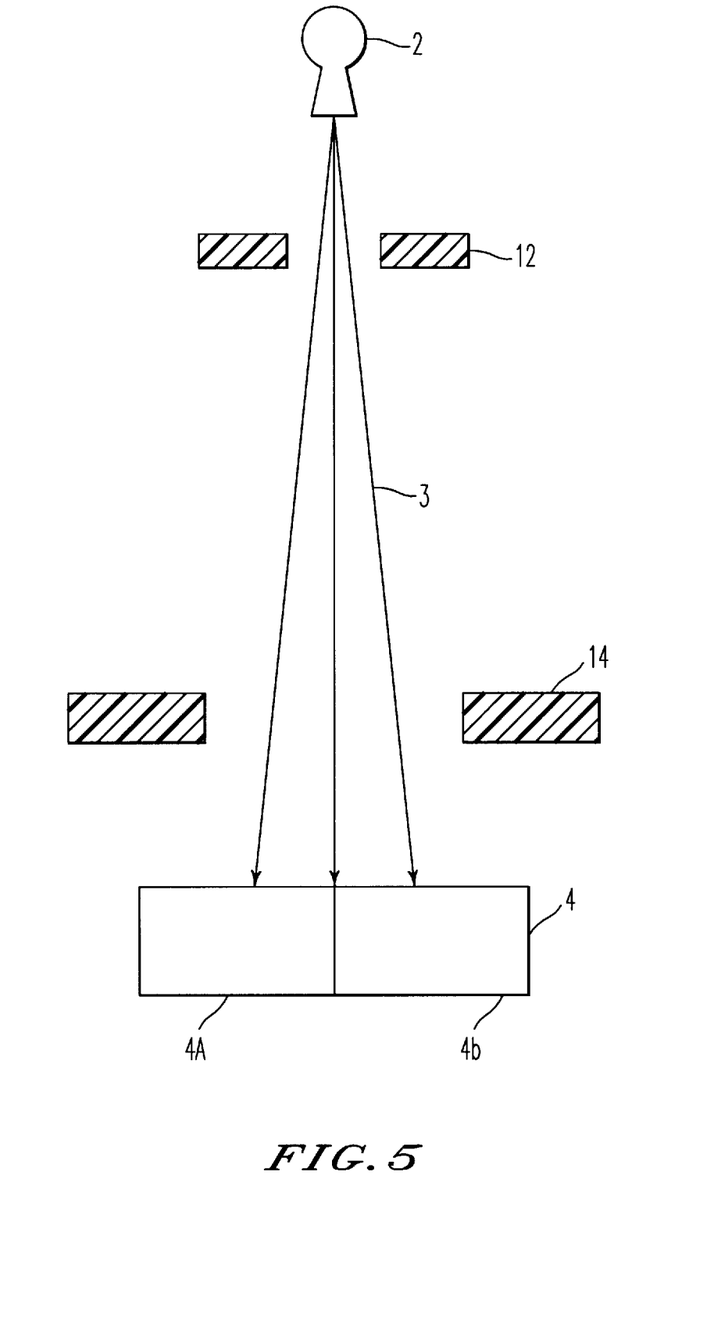
FIG. 5 is a diagram of an x-ray computed tomography device according to the present invention with a double slice detector.

Obviously, numerous modifications and variations of the present invention are possible in light of the above teachings. It is therefore to be understood that within the scope of the appended claims the invention may be practiced otherwise than as specifically described herein. For example, while the above described embodiment uses the third generation x-ray CT device employing a helical scan method, other generation x-ray CT devices are also acceptable to the present invention. Although the 180° and 360° interpolation processing methods have been described, the invention allows the use of interpolation where one can determine an effective slice thickness. As shown in FIG. 5, the present invention is also applicable to an x-ray computed tomography device, which comprises a double slice detector 4 having two detecting rows 4A and 4B formed by detecting elements having a plurality of channels and can change a slice thickness by the x-ray optical mechanism, and may employ a helical scan method. Further, the selected slice and effective slice do not have to be exactly equal. A range of approximately ±10% is acceptable.

What is claimed as new and is desired to be secured by Letters Patent of the United States is:

1. A device for controlling a helical scanning computed tomography device, comprising:
    a designated slice thickness input device;
    an effective slice thickness determination device connected to said input device;
    a memory storing data relating to a relationship between said designated slice thickness and an effective slice thickness connected to said effective slice determination device; and
    a designated slice thickness/effective slice thickness substantial equalization device connected to said effective slice thickness determination device.

2. A device as recited in claim 1, wherein said designated slice thickness/effective slice thickness substantial equalization device comprises:
    at least one of an adjustable x-ray slit device, a beam trimming device, and a scan pitch control device.

3. A device as recited in claim 2, wherein:
    said designated slice thickness/effective slice thickness substantial equalization device comprises said adjustable x-ray slit device, said beam trimming device, and said scan pitch control device; and
    said designated slice thickness/effective slice thickness equalization device substantially equalizes said designated slice thickness and said effective slice thickness by adjusting said adjustable x-ray slit device and setting said beam trimming device and said scan pitch control device to determined values obtained using said data stored in said memory.

4. A device as recited in claim 2, wherein:
    said designated slice thickness/effective slice thickness substantial equalization device comprises said adjustable x-ray slit device, said beam trimming device, and said scan pitch control device; and said designated slice thickness/effective slice thickness equalization device substantially equalizes said designated slice thickness and said effective slice thickness by adjusting said beam trimming device and setting said adjustable x-ray slit device and said scan pitch control device to determined values obtained using said data stored in said memory.

5. A device as recited in claim 2, wherein:

said designated slice thickness/effective slice thickness substantial equalization device comprises said adjustable x-ray slit device, said beam trimming device, and said scan pitch control device; and said designated slice thickness/effective slice thickness substantial equalization device substantially equalizes said designated slice thickness and said effective slice thickness by adjusting said scan pitch control device and setting said adjustable x-ray slit device and said beam trimming device to determined values obtained using said data stored in said memory.

6. A device as recited in claim 1, wherein said designated slice thickness/effective slice thickness substantial equalization device substantially equalizes said designated slice thickness and said effective slice thickness.

7. A device as recited in claim 6, wherein said designated slice thickness/effective slice thickness substantial equalization device substantially equalizes said designated slice thickness and said effective slice thickness to within approximately ±10%.

8. A device as recited in claim 1, wherein:

said input device comprises a designated slice thickness and interpolation processing method input device; and said designated slice thickness/effective slice thickness substantial equalization device substantially equalizes said designated slice thickness and said effective slice thickness based upon said designated slice thickness and said interpolation processing method.

9. A device as recited in claim 8, wherein said interpolation processing method is one of 180° and 360° interpolation processing methods.

10. A device as recited in claim 9, wherein:

when said interpolation processing method is said 180° interpolation processing method said designated slice thickness/effective slice thickness substantial equalization device reduces said designated slice thickness by approximately 10–20%; and when said interpolation processing method is said 360° interpolation processing method said designated slice thickness/effective slice thickness substantial equalization device reduces said designated slice thickness by approximately 30–40%.

11. A device as recited in claim 1, wherein said designated slice thickness/effective slice thickness substantial equalization device comprises an increasing ratio determination device.

12. A helical scanning computed tomography device, comprising:

an x-ray source;
an x-ray beam slit;
a beam trimmer;
an x-ray detector;
a memory storing data relating to a relationship between a designated slice thickness and an effective slice thickness;
a scan pitch adjustment device; and
an effective slice thickness determination and control device connected to said memory said x-ray beam adjustment device, said beam trimming device and said scan pitch adjustment device.

13. A device as recited in claim 12, wherein said detector is a double slice detector.

14. A device as recited in claim 12, wherein said effective slice thickness determination and control device substantially equalizes a designated slice thickness and an effective slice thickness of said computed tomography device by one of adjusting said x-ray beam slit and setting said beam trimmer and said scan pitch adjustment device to determined values;

adjusting said beam trimmer and setting said x-ray beam slit and said scan pitch adjustment device to determined values; and adjusting said scan pitch adjustment device and setting said x-ray beam slit and said beam trimmer to determined values.

15. In a method of operating a helical scanning computed tomography device, setting a designated slice thickness substantially equal to that of an effective slice thickness determined using a slice thickness of a reconstructed image.

16. In a method of operating a helical scanning computed tomography device, storing data relating to a relationship between a designated slice thickness and an effective slice thickness;

adjusting said designated slice thickness based upon an increasing ratio determined using said data.

17. A helical scanning x-ray computed tomography method, comprising:

selecting a slice thickness;
determining an effective slice thickness; and
substantially equalizing said slice thickness and said effective slice thickness.

18. A method as recited in claim 17, wherein substantially equalizing said slice thickness and said effective slice thickness comprises one of adjusting a scan pitch and adjusting an x-ray beam.

19. A method as recited in claim 18, wherein substantially equalizing said slice thickness and said effective slice thickness comprises one of:

adjusting a scan pitch while setting x-ray beam adjustment parameters to determined values; and adjusting said x-ray beam parameters while setting said scan pitch to a determined value.

20. A method as recited in claim 18, wherein adjusting said x-ray beam parameters comprises one of:

trimming said x-ray beam; and
passing said x-ray beam through an adjustable slit.

21. A method as recited in claim 17, wherein substantially equalizing said slice thickness and said effective slice thickness comprises using an increasing ratio.

22. A method as recited in claim 17, further comprising:

selecting an interpolation processing method;

wherein substantially equalizing said slice thickness and said effective slice thickness comprises using said slice thickness and said interpolation processing method.

23. A method as recited in claim 22, wherein substantially equalizing said slice thickness and said effective slice thickness comprises using an increasing ratio based upon selection of said interpolation processing method.

24. A method as recited in claim 22, comprising:

selecting one of 180° and 360° interpolation processing methods;

reducing said selected scan thickness by approximately 10–20% when said 180° interpolation processing method is selected; and reducing said selected scan thickness by approximately 30–40% when said 360° interpolation processing method is selected.

25. A method as recited in claim 17, comprising equalizing said slice thickness and said effective slice thickness to within approximately ±10%.

26. A method as recited in claim 16, comprising:

designating said slice thickness substantially at a rotational center of said computed tomography device.

27. A method as recited in claim 16, comprising:

performing a scan using said adjusted slice thickness; and obtaining a reconstructed image having a slice thickness substantially equal to said designated slice thickness.

28. A method as recited in claim 17, comprising:

determining said effective slice thickness using reconstructed image data.

29. A method as recited in claim 17, wherein substantially equalizing comprises:

determining a relationship between said slice thickness and said effective slice thickness; and substantially equalizing said slice thickness and said effective slice thickness using said relationship.

30. A method as recited in claim 29, comprising:

storing in said device said relationship between said slice thickness and said effective slice thickness.

31. A method as recited in claim 17, comprising:

storing a relationship between said slice thickness and said effective slice thickness; and conducting a scan using said equalized slice thickness.

32. A method as recited in claim 17, comprising:

performing a scan using said effective slice thickness; and obtaining a reconstructed image having a slice thickness substantially equal to said slice thickness selected in said selecting step.

* * * * *